United States Patent
Yamashita et al.

[11] Patent Number: 6,030,641
[45] Date of Patent: Feb. 29, 2000

[54] SUSTAINED RELEASE CAPSULE AND METHOD FOR PREPARING THE SAME

[75] Inventors: Sadaji Yamashita; Seiki Harada, both of Kanagawa-ken, Japan

[73] Assignee: Uni Colloid Kabushiki Kaisha, Kanagawa-ken, Japan

[21] Appl. No.: 09/080,374

[22] Filed: May 12, 1998

[30] Foreign Application Priority Data

Jun. 3, 1997 [JP] Japan .................................. H9-159337

[51] Int. Cl.⁷ .............................. A61K 9/48; A61K 9/56
[52] U.S. Cl. .................... 424/451; 424/456; 424/457; 424/458; 424/459; 424/460; 424/461; 424/462; 424/463; 424/491
[58] Field of Search ...................... 424/451, 456, 424/457, 458, 459, 460, 461, 462, 463, 491

[56] References Cited

U.S. PATENT DOCUMENTS

| | | | |
|---|---|---|---|
| 4,683,092 | 7/1987 | Tsang | 264/4.3 |
| 4,851,394 | 7/1989 | Kubodera | 514/54 |
| 5,576,022 | 11/1996 | Yang et al. | 424/472 |
| 5,597,564 | 1/1997 | Ying et al. | 424/94.65 |
| 5,882,715 | 3/1999 | Nielsen et al. | 427/2.16 |

FOREIGN PATENT DOCUMENTS

| | | |
|---|---|---|
| 0225189 | 6/1987 | European Pat. Off. . |
| 6-47530 | 10/1991 | Japan . |
| 647530 | 10/1991 | Japan . |
| 95/06464 | 3/1995 | WIPO . |

OTHER PUBLICATIONS

Database WPI—Section Ch, Week 8845, Derwent Publications Ltd., London, GB; Class B07, AN 88–320115 & JP 63 238015 A (Morishita Jintan KK) Oct. 4, 1988—abstract.
Database WPI—Section Ch, Week 8351—Derwent Publications Ltd., London, GB; Class A96, AN 83–847880 & JP 58 194810 A (Morishita Jintan KK) Nov. 12, 1983—abstract.
Database WPI—Section Ch, Week 8346—Derwent Publications Ltd., London, GB; Class A96, AN 83–818130 & JP 58 172313 A (Morishita Jintan KK) Oct. 11, 1983—abstract.
Database WPI—Section Ch, Week 8643—Derwent Publications Ltd., London, GB; Class A96, AN 86–282502 & JP 61 207328 A (Taisho Pharm Co Ltd) Sep. 13, 1986 –abstract.
Database WPI—Section Ch, Derwent Publications Ltd., London, GB; Class B00, AN 66–08954F & CA 669 954 A (Organon NV)—abstract. 1966.
Database WPI—Section Ch, Week 8025—Derwent Publications Ltd., London,, GB Class A11, AN 80–43328C & BE 881 462 A (Heumann Co L), May 16, 1980—abstract.
Database WPI—Section Ch, Week 8741—Derwent Publications Ltd., London, GB; Class A96, AN 87–285591—abstract & EP 0 240 581 A (Scherer R.P. GmbH).

*Primary Examiner*—Thurman K. Page
*Assistant Examiner*—Lakshmi Channavajjala
*Attorney, Agent, or Firm*—Jordan and Hamburg LLP

[57] ABSTRACT

A sustained release capsule in which an outer surface of a hard capsule mainly composed of gelatin and containing a physiologically active substance is uniformly covered with a film material comprising a natural polysaccharide/polyhydric alcohol composition which is prepared by uniformly kneading at least one natural polysaccharide selected from the group consisting of carrageenan, alginic acid, salts of alginic acid, derivatives of alginic acid, agar, locust bean gum, guar gum, pectin, amylopectin, xanthane gum, glucomannan, chitin and pullulan in at least one system selected from the group consisting of polyhydric alcohols, sugar alcohols, monosaccharides, disaccharides, trisaccharides and oligosaccharides. A capsule formed merely of the natural polysaccharide/polyhydric alcohol composition swells and is permeated by water. It is poor in shape-retaining properties, failing to retain its shape in the stomach, although it is nondigestive. However, the gelatin capsule covered with this composition prevents digestion of gelatin, can be conveyed to the small intestine without deactivation of the physiologically active substance contained therein, and can gradually release the contents in the intestine at a speed according to its purpose, so that it is useful for the effective utilization of the physiologically active substance.

14 Claims, No Drawings

SUSTAINED RELEASE CAPSULE AND METHOD FOR PREPARING THE SAME

FIELD OF THE INVENTION

The present invention relates to a sustained release capsule which prevents a physiologically active substance from being decomposed and deactivated in the stomach and gradually releases the substance at any site from the small intestine to the large intestine, and a method for preparing the same.

BACKGROUND OF THE INVENTION

Previously, means such as oral administration, anal administration and injection have been adopted in the administration of physiologically active substances to the human body. For the oral administration, the substances are used in the form of capsules, tablets, granules etc. The substances orally administered, however, tend to be decomposed or deactivated by the action of a strong acid or an enzyme in the stomach before reaching the small intestine.

The stomach is an organ in which food ingested is digested. Carbohydrates in the food are decomposed to glucose through dextrin, oligosaccharide and maltose. Proteins are decomposed to amino acids through polypeptides, and fats are decomposed to glycerin and fatty acids. Although all these decomposition reactions may not always take place in the stomach, the physical, chemical and enzymic decomposition action in the stomach is considerably vigorous. It converts the food to a semiliquid rice gruel-like digest. As a result, the digestion in the duodenum and the digestion and absorption in the small intestine easily proceed. In particular, the physical decomposition action by the peristalsis of the stomach and the chemical decomposition action by the strong acidity of hydrochloric acid are non-selective, and considerably vigorous.

This nonselective, physical and chemical decomposition action is a negative factor with respect to most of the physiologically active substances administered orally. That is to say, many medicines and physiologically active substances are decomposed and deactivated in the stomach, and the efficacy thereof is reduced abruptly.

Furthermore, the digest is absorbed by the small intestine. The physiologically active substances administered orally are also digested in the stomach, carried to the entrance of the small intestine, and absorbed rapidly thereby, resulting in a rapid increase in the amount of the substances in the blood. It is however preferred that the speed of releasing the physiologically active substances from capsules is adjusted even in the small intestine, depending on their purpose. That is to say when it is desired, for medicines to act directly on the large intestine, such as chemotherapeutics against cancer of the large intestine, the speed should be adjusted so that they can reach the large intestine with almost no absorption of the medicines by the small intestine, when it is desired that physiologically active substances be swiftly absorbed by the small intestine, the speed should be adjusted so that they can be promptly released from capsules in the small intestine.

A technique of enclosing a physiologically active substance in a hard capsule formed of gelatin and coating an outer surface of the capsule with a specific protein resistant to digestion by gastric juice has also been proposed. Even according to this technique, however, the capsule is digested in the stomach.

The present inventors have disclosed a technique comprising making a capsule perforated with numerous holes which is formed of a viscous solution obtained by dissolving a natural polysaccharide/polyhydric alcohol composition in water, enclosing in the capsule a physiological active substance acting on the intestines, and coating the capsule with an edible hardened fat having a melting point of 35° C. or above, in Japanese Unexamined Patent Publication No. 3-232815.

However, the capsule formed of the natural polysaccharide/polyhydric alcohol composition is poor in rigidity although it has flexibility, and has a tendency to physically break by the vigorous peristalsis of the stomach and intestines. In addition, the capsule perforated with numerous holes is very difficult to be produce on a commercial scale.

A protecting means has been demanded for allowing a physiologically active substance to act efficiently at any site from the small intestine to the large intestine, when it is orally administered. It must pass through the stomach without damage, prevent a loss in efficacy thereof in the stomach. That is to say, a capsule is desired which is scarcely dissolved in the stomach and can gradually release the physiologically active substance while passing from the small intestine to the large intestine.

SUMMARY OF THE INVENTION

According to the present invention, there is provided a sustained release capsule in which an outer surface of a hard capsule mainly composed of gelatin is uniformly covered with a film material comprising a natural polysaccharide/polyhydric alcohol composition which is prepared by uniformly kneading at least one natural polysaccharide selected from the group consisting of carrageenan, alginic acid, salts of alginic acid, derivatives of alginic acid, agar, locust bean gum, guar gum, pectin, amylopectin, xanthane gum, glucomannan, chitin and pullulan in at least one system selected from the group consisting of polyhydric alcohols, sugar alcohols, monosaccharides, disaccharides, trisaccharides and oligosaccharides. When a physiologically active substance is enclosed in the capsule, a large portion of the physiologically active substance remains therein after passing through the stomach, and most of the remainder is gradually released therefrom at any site from the small intestine to the large intestine.

That is to say, in the present invention, the sustained release capsule is prepared by uniformly covering the outer surface of the known hard capsule mainly formed of gelatin with the film material comprising the natural polysaccharide/polyhydric alcohol composition. Enzymes which digest natural high polymeric polysaccharides are not present in the digestive tracts of the human body. Further, the film material comprising the natural polysaccharide/polyhydric alcohol composition is semipermeable, so that it becomes possible to gradually release the physiologically active substance contained in the capsule at any site from the small intestine to the large intestine without its decomposition or deactivation, which allows the substance to act very effectively on any site from the small intestine to the large intestine.

DETAILED DESCRIPTION OF THE INVENTION

The physiologically active substances used in the present invention mean substances exhibiting physiological activity in a broad sense, including food and medicines acting usefully on organisms.

The medicines as used herein include drugs efficacious against various kinds of diseases such as circulatory diseases, for example, cardiovascular diseases and diseases involving high blood pressure, respiratory diseases, gastrointestinal diseases, malignant tumors such as cancer, and diseases caused by endocrine metabolic errors such as diabetes.

Additionally, examples of the physiological active substances in a broad sense include various hormones such as pituitary hormone, insulin, glucagon, melatonin, and cytokinin, hormone-like substances; such as prostaglandin, caropeptide and kinin, and neurotransmitters, such as catecholamine, indoleamine and acetylcholine and substances derived from marine organisms occurring in nature. Further, examples thereof also include useful intestinal bacteria such as Bifidobacterium and Lactobacillus, and nutrient auxiliary food such as royal jelly, ginseng, chitosan, nanpao, taurine, lecithin, flavonoids, chlorella, fermented soybean kinase and chondroitin, as well as various vitamins and minerals.

The natural polysaccharide/polyhydric alcohol composition is obtained by uniformly kneading at least one natural polysaccharide selected from the group consisting of carrageenan, alginic acid, salts of alginic acid, derivatives of alginic acid, agar, locust bean gum, guar gum, pectin, amylopectin, xanthane gum, glucomannan, chitin, and pullulan in at least one system selected from the group consisting of polyhydric alcohols in a narrow sense, such as glycerin, ethylene glycol, propylene glycol and diglycerin, sugar alcohols, monosaccharides, disaccharides, trisaccharides and oligosaccharides. In the polyhydric alcohol system, the composition can be used as such or as a concentrated solution of 70% or more when it is liquid, and as an aqueous solution of 65% to 95%, preferably 70% to 90% when it is solid.

A viscous aqueous solution can be obtained by adjusting the concentration of an aqueous solution of the above-mentioned natural polysaccharide/polyhydric alcohol composition to a specified concentration and heating the resulting solution. The coating film strength can be increased by adding an alkali.

Commercially available shape-retaining capsules made of gelatin or mainly composed of gelatin can be used as the hard capsules.

The sustained release capsule of the present invention is obtained by enclosing a specified amount of the physiologically active substance in the hard capsule, allowing the viscous solution of the natural polysaccharide/polyhydric alcohol composition described above to adhere to the hard capsule, and then drying it. When the viscous solution of the composition is allowed to adhere to the hard capsule, dipping, coating or other means can be used.

The amount of the natural polysaccharide/polyhydric alcohol composition applied to the outer surface of the hard capsule varies depending on the kind of capsule and physiologically active substance contained therein. However, the amount of the composition is generally from 50 parts to 1000 parts by weight, and preferably from 100 parts to 500 parts by weight per 100 parts by weight of gelatin.

When a thin film of a fat having a melting point of 40° C. or above, such as hardened oil, is formed on the outer surface of the gelatin capsule prior to coating thereof with the natural polysaccharide/polyhydric alcohol composition, the release or deactivation of the contents of the capsule in the stomach can be more inhibited. In order to form the thin film of hardened oil, an emulsifying agent such as lecithin and water or a lower alcohol are added to the fat, followed by emulsification. Then, the hard capsule is covered with the resulting emulsion by coating or spraying, and thereafter the solvent is removed by drying, or the hard capsule can also be directly immersed in the fat.

It is also effective to provide the fat layer on an outer surface of the natural polysaccharide/polyhydric alcohol composition layer.

In some cases, it is also possible to further provide a particular protein film on the outer surface of the capsule having the natural polysaccharide/polyhydric alcohol composition film to protect the capsule. The types of particular protein include corn protein and wheat protein containing a large amount of gluten. The formation of the protein film not only permits an improvement in digestive resistance of the capsule in the stomach, but also heightens the commercial value due to the surface treatment.

The term "being uniformly covered" as used herein means that there is no perforation or crack on the surface of the capsule, although some unevenness may be allowed to exist thereon. The film of the natural polysaccharide/polyhydric alcohol composition utilizes the permeability of the material for the purpose of gradually digesting the internal gelatin by the digestive juice such as the gastric juice and the pancreatic juice. Accordingly, the presence of the perforation or crack is unfavorable because it causes prompt elution of the contents.

The natural polysaccharide/polyhydric alcohol composition of the present invention is not digested, but has semipermeability. The natural polysaccharide/polyhydric alcohol composition swells in the presence of sufficient water in the stomach, and allows the gastric juice to pass therethrough in cooperation with the semipermeability, which brings the juice into contact with the gelatin of the capsule. Consequently, when the composition layer is thin or not sufficiently dense, the gelatin may be digested in the stomach to release the contents. The hard capsule made of gelatin is merely a support for the natural polysaccharide/polyhydric alcohol composition, and the physiologically active substance is released through the composition layer as the capsule passes through the stomach and intestines. The capsule material is ultimately crushed to a thin film piece.

EXAMPLES

Examples 1 and 2 and Comparative Examples 1 and 2

(1) Preparation of Covering Solution Comprising Natural Polysaccharide/Polyhydric Alcohol Composition

| | |
|---|---|
| Carrageenan | 60 parts by weight |
| Glucomannan | 20 parts by weight |
| Guar Gum | 10 parts by weight |
| Alginic Acid | 10 parts by weight |

These substances were uniformly mixed, and 30 parts by weight of glycerin was added thereto and kneaded at room temperature (20° C.±10° C.) to obtain a somewhat wet powdery natural polysaccharide/polymeric alcohol composition. Three parts by weight of this composition were dissolved in 97 parts by weight of water to obtain a viscous aqueous solution.

(2) Preparation of Sustained Release Capsules

Gelatin capsules in which *Bifidobacterium longum* was enclosed were covered with the viscous aqueous solution of the natural polysaccharide/polyhydric alcohol composition prepared in (1), and dried to obtain the sustained release capsules of the present invention.

The gelatin capsules used above were Gelatin Capsule No. 1 manufactured by Warner Lambert Co., Ltd.

Bifidus "100" longum ( $200 \times 10^8$ viable cells /g) manufactured by Amano Pharmaceutical Co., Ltd. was used as *Bifidobacterium longum* and 0.6±0.05 g thereof was enclosed per capsule.

The capsules were each covered with the natural polysaccharide/polyhydric alcohol composition in an amount of 130 g per 100 g of gelatin by the use of a full automatic film coating device (New High Coater HCT-48N manufactured by Freund Co.) (Example 1).

Surfaces of the capsules obtained in Example 1 were each covered with corn protein at a rate of 30 g per 100 g of gelatin to obtain the capsules of Example 2.

(3) Elution Test Solution (Addition of Enzyme)

Elution test solutions were prepared according to the Pharmacopoeia of Japan, thirteenth edition, general test methods 159 to 162. The pH of a first solution was approximately adjusted to that of the stomach, and the pH of a second solution to that of the intestines. Further, in order to approximate the actual conditions of the stomach and intestines, a gastric secretion digestive enzyme, pepsin (pepsin 1:10,000 manufactured by Wako Pure Chemical Industries Ltd.) was added to the first solution.

First Solution: Water was added to 2.0 g of NaCl, 7.0 ml of concentrated HCl and 1.0 g of pepsin to make the total volume 1000 ml.

Second Solution: Pancreatin (manufactured by Wako Pure Chemical Industries Ltd.) was added to the second solution according to the formula of an artificial intestinal juice described in "*Yakugaku Dai-jiten* (Grand Dictionary of Pharmacy)" (edited by Nippon Kogyo Gijutsu Renmei). That is to say, water was added to 2.8 g of Pancreatin and 15.0 g of $NaHCO_3$ to make the total volume 1000 ml.

(4) Method of Elution Test

A beaker into which 100 ml of the first solution was poured was placed in a warm bath maintained at 37±2° C., and the 10 capsules prepared in (2) were put into the beaker, followed by continuous shaking for 2 hours (the general residence time in the stomach).

A beaker into which 400 ml of the second solution was poured was placed in a warm bath maintained at 37±2° C., and the five capsules tested for the first solution were put into the beaker, followed by continuous shaking for 16 hours (a time obtained by subtracting 2 hours from 18 hours, the average residence time of food in the digestive tract).

(5) Results of Test

The dry weight of the capsules was weighed after completion of the test in the first solution of the elution test solutions and after a total elution time of 16 hours in the second solution, and the residual ratios of the contents were calculated. As a result, Examples 1 and 2 both showed 92% to 94% by weight after the elution test of the first solution, and 12% to 15% by weight after the elution test of the second solution.

A similar test was carried out as Comparative Example 1 in which gelatin capsules containing *Bifidobacterium longum* were prepared similarly to Example 1 with the exception that gelatin was covered with nothing. In Comparative Example 2 capsules containing *Bifidobacterium longum* were prepared similarly to Example 1 with the exception that gelatin was covered with an equivalent mixture of corn protein and wheat protein at a rate of 130 g per 100 g of gelatin in place of the natural polysaccharide/polyhydric alcohol composition. The capsules of both Comparative Examples 1 and 2 immediately dissolved in the first solution leaving no remains thereof. For each of the examples, after completion of the test in the first solution of the elution test solutions, and after a total elution time of 8 hours (2 hours+6 hours) and a total elution time of 18 hours (2 hours+16 hours) in the second solution, respectively, the contents of the capsules were weighed, and the residual ratios thereof were calculated. Results thereof are shown in Table 1.

The results prove that the capsules of the present invention are high in resistance to gastric juice and also to intestinal juice.

Examples 3 and 4

(1) Preparation of Sustained Release Capsule

Sustained release capsules containing *Bifidobacterium longum* of Example 3 were obtained in the same manner as in Example 1 with the exception that,

| Carrageenan | 20 parts by weight |
| --- | --- |
| Glucomannan | 30 parts by weight |
| pullulan | 20 parts by weight |
| Guar Gum | 10 parts by weight |
| Alginic Acid | 20 parts by weight were used. |

The average weight of gelatin per capsule was 0.079 g, the average weight of the natural polysaccharide/polyhydric alcohol composition per capsule was 0.188 g, and the film thickness was approximately 400 μm. Further, in Example 4, sustained release capsules containing Lactobacillus bifidus were obtained by covering the surfaces of the capsules with films of hardened oil and subsequently covering them with the natural polysaccharide/polyhydric alcohol composition in the same manner as in Example 3. Hardened Oil MR-60 (manufactured by Miyoshi Oil & Fat Co., Ltd., melting point: 60° C.) was used, and emulsified with lecithin. The resulting emulsion was sprayed, and water was removed by drying. The thickness of the fat layer was estimated to be from 50 μm to 70 μm.

In Examples 3 and 4, the number of *Bifidobacterium longum* cells in the capsules was determined. With respect to the first solution, the viable cell count was measured after 2 hours. With respect to the second solution, the number of viable cells eluted in the shaken solution was measured.

(2) Method of Measuring the Viable Cell Count

The measurement was carried out by the use of a BL agar medium as a culture medium (manufactured by Eiken Chemical Co., Ltd.) and Gas Pack 150™ (manufactured by Becton Dickinson and Co., Ltd.).

(3) Results of Test

The viable cell count was measured after testing for 2 hours in the first solution. Further, one of the capsules was transferred to the second solution to continue the test, and the number of viable cells released in the second solution was measured after respective total test times of 6 hours (2 hours +4 hours) and 18 hours (2 hours+16 hours). Following the measurement of the viable cell count after a total test time of 6 hours, the capsule was transferred to a fresh second solution, and the test was continued. Then, the number of viable cells released in the test solution after a total test time of 18 hours was measured. Results thereof are indicated in Table 1. The capsules of Examples 3 and 4, which had been stirred in the digestive juice for a total time of 18 hours, were deformed to flat and undefined floating matter. No remains of the capsules of Comparative Examples 1 and 2 were recovered after testing.

Table 1 indicates that the sustained release capsules of the present invention have resistance to pancreatin and are ideal sustained release capsules which gradually release *Lactobacillus bifidus* in the small intestine.

In these Examples, *Bifidobacterium longum* was selected as a representative of a physiologically active substances, because it is an organism, and very sensitive to temperature, pH and water.

Accordingly, if the effectiveness of the capsules is confirmed with *Bifidobacterium longum*, we can assume that the capsules are naturally effective for foods and drugs as physiologically active substances, which are not-organisms.

Examples 5 to 7

Influence of Film Thickness of Natural Polysaccharide/Polyhydric Alcohol Composition Sustained release capsules differing in thickness were prepared in the same manner as in Example 4 with the exception that the film thickness of the natural polysaccharide/polyhydric alcohol composition was 200 μm (Example 5), 500 μm (Example 6) and 800 μm (Example 7). These capsules were shaken in the first solution for 2 hours under the same conditions as in Examples 3 and 4, and subsequently shaken in the second solution for 16 hours. That is to say, the dry weight of the capsules was determined at the start of the experiment, after shaking in the first solution for 2 hours, after shaking in the second solution for 4 hours and after shaking in the second solution for 16 hours, respectively. Results thereof are shown in Table 2.

Table 2 reveals that the release time of the contents in the capsules can be controlled by adjusting the film thickness of the natural polysaccharide/polyhydric alcohol composition.

Example 8

Human insulin (manufactured by Wako Pure Chemical Industries Ltd.) was mixed with hydrophilic cellulose as a filler, and the capsules were charged with the resulting mixture so as to give 25 i.u. of human insulin per capsule. The capsules thus prepared were covered with hardened oil and the natural polysaccharide/polyhydric alcohol composition in the same manner as in Example 6, and the resulting capsules were tested in the same manner as in Example 6. The dry weight of one capsule after completion of the test in the first solution was about 90% of the initial weight, and the dry weight after shaking in the second solution for 4 hours was about 40% of the initial weight. The capsules, after shaking in the second solution for 16 hours, were deformed to flat and undefined floating matter.

TABLE 1

| Kind of Capsule | Viable Cell Count in Capsule after 2 hrs. (First Liquid) | Total Number of Viable Cells Released from One Capsule during 2–6 hrs. (Second Liquid) | Total Number of Viable Cell Released from One Capsule during 6–18 hrs. (Second Liquid) |
| --- | --- | --- | --- |
| Example 3 (Covered with polysaccharide) | 4.8 × 10$^8$ | 1.8 × 10$^8$ | 0.9 × 10$^8$ |
| Example 4 (Covered with polysaccharide after covered with hardened oil) | 5.2 × 10$^8$ | 2.3 × 10$^8$ | 1.1 × 10$^8$ |
| Comparative Example 1 (Not covered) | Immediately dissolved | — | — |
| Comparative Example 2 (Covered with protein) | Soon dissolved | — | — |

TABLE 2

| | Weight of Capsule (g) | | | |
| --- | --- | --- | --- | --- |
| Film Thickness | At Start of Experiment | After 2 hrs. (First Liquid) | After 6 hrs. (Second Liquid) | After 18 hrs. (Second Liquid) |
| Example 5 (200 μm) | 0.82 | 0.53 | 0.07 | 0.05 |
| Example 6 (500 μm) | 0.97 | 0.75 | 0.37 | 0.19 |
| Example 7 (800 μm) | 1.12 | 1.01 | 0.58 | 0.36 |

What is claimed is:

1. A sustained release capsule, comprising:
   an encapsulating structure which is shape-retaining and which is comprised of, gelatin the encapsulating structure being of sufficient hardness to resist physical degradation due to stomach peristalsis, the encapsulating structure presenting an outer surface; and
   a coating of a film material uniformly covering the outer surface of the encapsulating structure, the film material being a polysaccharide/polyhydric alcohol composition which is prepared by uniformly kneading at least one polysaccharide selected from the group consisting of carrageenan, alginic acid, salts of alginic acid, derivatives of alginic acid, agar, locust bean gum, guar gum, pectin, amylopectin, xanthane gum, glucomannan, chitin and pullulan in at least one system selected from the group consisting of polyhydric alcohols, sugar alcohols, monosaccharides, disaccharides, trisaccharides and oligosaccharides.

2. The sustained release capsule of claim 1, further comprising a fat layer having a melting point of 40° C. or above interposed between the outer surface of the inner capsule and the coating of the polysaccharide/polyhydric alcohol composition.

3. The sustained release capsule of claim 1, further comprising a fat layer having a melting point of 40° C. or above on an outer surface of the polysaccharide/polyhydric alcohol composition.

4. The sustained release capsule of claim 1, further comprising a protein film on the polysaccharide/polyhydric alcohol composition.

5. The sustained release capsule of claim 1, wherein the film material further comprises an alkali.

6. A method for preparing a sustained release capsule, comprising:
   inserting a physiologically active substance in an encapsulating structure which is shape-retaining and which is comprised of gelatin, the encapsulating structure being of sufficient hardness to resist physical degradation due to stomach peristalsis;

uniformly covering said encapsulating structure with a film material of a polysaccharide/polyhydric alcohol composition by dipping the encapsulating structure in the polysaccharide/polyhydric alcohol composition, coating the encapsulating structure with the polysaccharide/polyhydric alcohol composition, or spraying the encapsulating structure with the polysaccharidelpolyhydric alcohol composition, the polysaccharide/polyhydric alcohol composition being prepared by uniformly kneading at least one polysaccharide selected from the group consisting of carrageenan, alginic acid, salts of alginic acid, derivatives of alginic acid, agar, locust bean gum, guar gum, pectin, amylopectin, xanthane gum, glucomannan, chitin and pullulan in at least one system selected from the group consisting of polyhydric alcohols, sugar alcohols, monosaccharides, disaccharides, trisaccharides and oligosaccharides; and drying the film material on the encapsulating structure.

7. The sustained release capsule of claim 1, wherein the amount of the polysaccharide/polyhydric alcohol composition is about 50 parts to about 1000 parts by weight per about 100 parts by weight of gelatin.

8. The sustained release capsule of claim 1, wherein the amount of the polysaccharide/polyhydric alcohol composition is about 100 parts to about 500 parts by weight per about 100 parts by weight of gelatin.

9. The sustained release capsule of claim 1, wherein the polysaccharide in the polysaccharide/polyhydric alcohol composition is about 60 parts by weight carrageenan, about 20 parts by weight glucomannan, about 10 parts by weight guar gum and about 10 parts by weight alginic acid.

10. The sustained release capsule of claim 1, wherein the polysaccharide in the polysaccharide/polyhydric alcohol composition is about 20 parts by weight carrageenan, about 30 parts by weight glucomannan, about 20 parts by weight pullulan, about 10 parts by weight guar gum and about 10 parts by weight alginic acid.

11. The sustained release capsule of claim 1, wherein the thickness of the film of the polysaccharide/polyhydric alcohol composition is about 200 microns.

12. The sustained release capsule of claim 1, wherein the thickness of the film of the polysaccharide/polyhydric alcohol composition is about 500 microns.

13. The sustained release capsule of claim 1, wherein the thickness of the film of the polysaccharide/polyhydric alcohol composition is about 800 microns.

14. The method of claim 6, wherein the physiologically active substance is at least one substance selected from the group consisting of food, medicine, hormones, neurotransmitters, Bifidobacterium, Lactobacillus, vitamins and minerals.

* * * * *